June 9, 1936. S. POULSEN Plant Pat. 182
ROSE
Filed Jan. 9, 1936
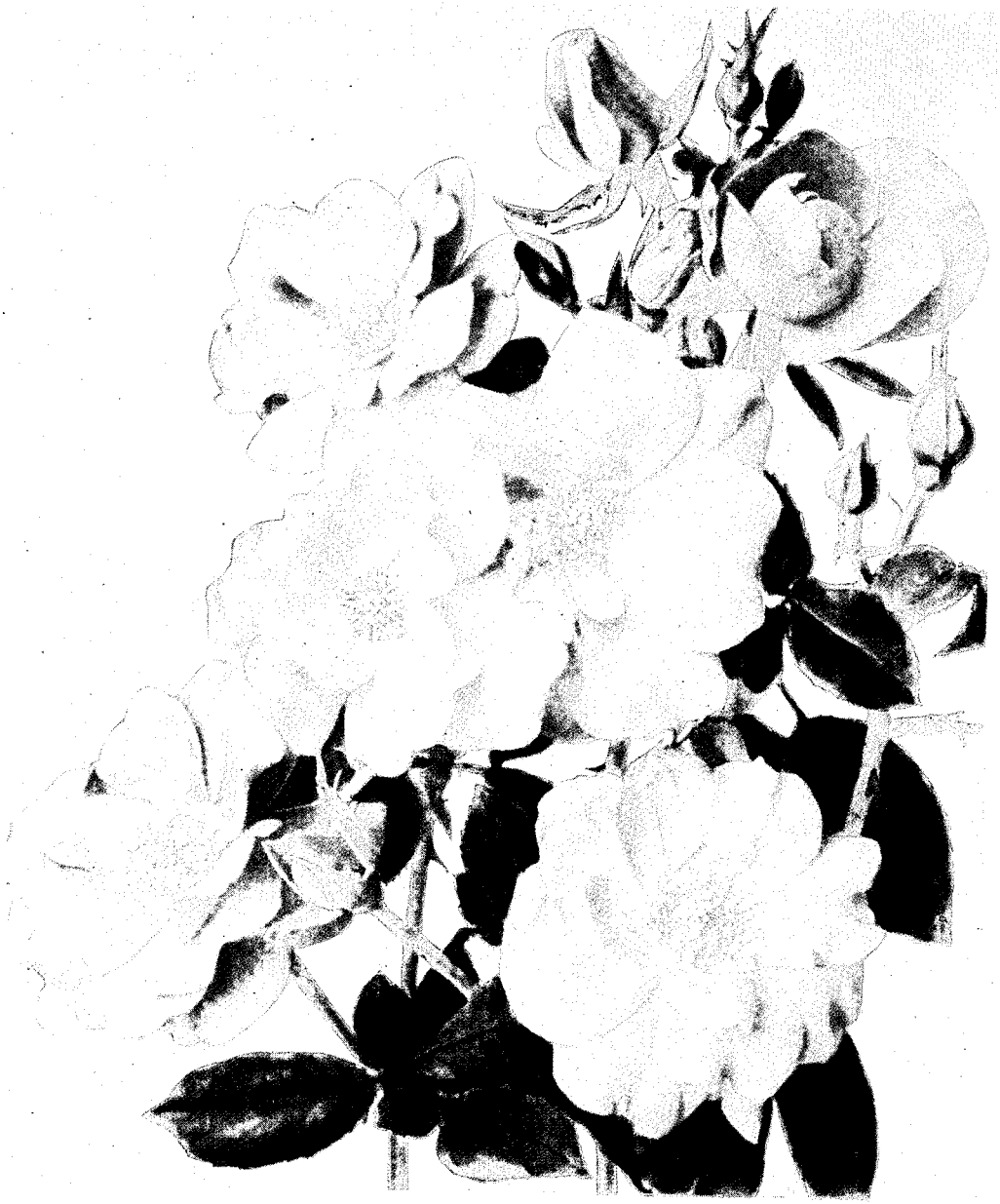
Inventor
S. Poulsen
By Robb & Robb
Attorneys Patented June 9, 1936

Plant Pat. 182

UNITED STATES PATENT OFFICE

182

ROSE

Svend Poulsen, Copenhagen, Denmark, assignor to Jackson and Perkins Company, Newark, N. Y.

Application January 9, 1936, Serial No. 58,387
In Denmark March 10, 1934

1 Claim. (Cl. 47—61)

The present invention relates to a new and distinct variety of rose plant produced from crossing the hybrid polyantha "Ingar Olsson" with an unnamed polyantha and hybrid tea seedling, with a view of creating a new type of bedding rose.

This origination constitutes a new addition to the commercially known "Poulsen Strain", marked as to important distinctions by retention of the hardiness and inflorescence of a polyantha with blooms nearly of the type and quality of the hybrid tea.

From its parents this new variety has inherited the characteristics of a hybrid tea, namely the full sized blooms, the long ovoid buds, the moderate fragrance and foliage in combination with the qualities of the true polyantha such as hardiness, vigorous growth and continuity of flowering until late autumn.

A further important feature of this new rose resides in its great resistance to all kinds of weather, such as burning sun, cold and rain, and by reason of the fact that it is mildew proof, a strong grower and healthy, it is ideal as a first class bedding rose.

In respect to color, it is markedly distinct, in that in one and the same bloom the color runs from bright crimson red to velvet-like red and this color does not fade and does not burn in the sun.

Asexual reproduction has proved these characteristics to be fixed.

The following is a detail description of this new variety, color designations being in accord with the Gravereaux color chart:—

Parentage:

*Seed parent.*—"Ingar Olsson".

*Pollen parent.*—Unnamed polyantha and hybrid tea seedling.

Classification:

Polyantha hybrid.

*Flower*

Blooming habit:

Continuous.

Bud:

*Size.*—Medium.

*Form.*—Long, ovoid. Unaffected by wet or hot weather.

*Color.*—When sepals first divide—scarlet crimson. When petals begin to unfurl—crimson. When half blown:

*Inside of petals.*—Scarlet crimson.

*Reverse of petals.*—Deeper tone.

*Sepals.*—Smooth, branched; curl back when bud unfurls.

*Calyx.*—Shape—funnel. Size—small. Aspect—smooth. Odor when rubbed—none.

*Peduncle.*—Length—medium. Aspect—smooth. Color—medium green. Strength—stiff, heavy.

*Opening.*—Opens well and is not affected by adverse conditions.

Bloom:

*Size.*—Large, average size when fully expanded 3" to 3½".

*Borne.*—In irregular clusters.

*Stems.*—Medium length, strong.

*Form.*—When first open, cupped; flattens when fully opened.

*Petalage.*—Semi-single (two rows of petals). Number of petals under normal conditions 10 to 15.

*Color.*—Center of flower—scarlet crimson. Outer petals—same. Base of petals (aiglet)—paling some. Inside of petal—scarlet crimson. Reverse of petals—slightly darker. General tonality from a distance—scarlet crimson.

*Variegations.*—None.

*Discoloration.*—General tonality at end of first day—crimson. Second day—scarlet crimson. Third day—scarlet.

Petals:

*Texture.*—Thick; unaffected by wet or hot weather.

*Appearance.*—Inside—velvety. Outside—satiny.

*Form.*—Round, slightly scalloped.

*Arrangement.*—Irregular; petaloids in center few and small.

*Persistence.*—Drop off cleanly.

*Fragrance.*—Moderate. Nature—"Old Rose perfume" (Centifolia).

*Lasting quality.*—On plant and as cut flower, very long.

Genital organs:

*Stamens, anthers.*—Large, many. Color—yellow. Arrangement—regular around styles.

*Stamens, filaments (threads).*—Long. Color—yellow.

*Pollen.*—Gold yellow.

*Styles.*—Bunched, even medium length, heavy.

*Stigmas.*—white.

*Ovaries.*—All enclosed in calyx.

Fruit:

Variety is seldom fertile with its own pollen.

*Form.*—Round.

*Aspect.*—Smooth.

*Color at maturity.*—Scarlet red.
*Sepals.*—Caducous (soon falling).

*Plant*

Form:
Bush.
Growth:
Vigorous, branching.
Foliage:
Generally five, sometimes seven leaflets.
*Size.*—Medium.
*Quantity.*—Normal.
*Color.*—*New foliage*—Upper side—dark green. Under side—lighter green.
*Old foliage*—Upper side—dark green. Under side—light green.
*Shape.*—Oval pointed.
*Texture.*—Upper side—leathery. Under side—smooth. Ribs and veins—ordinary.
*Edge.*—Serrated (saw toothed).
*Serrations.*—Single, small.
*Rachis.*—Color reddish; underside smooth.
*Stipules.*—Medium length, smooth.
*Disease resistance.*—Resistant.

Wood:
*New wood.*—Color—dark green. Bark—smooth.
*Old wood.*—Color—green. Bark—smooth.
Thorns: (Divided into thorns, prickles, and short needles).
*Thorns.*—Quantity—on main stalks from base, ordinary; on laterals from stalk, few. Form—broad base, medium length, hooked downward. Color when young—red. Position—irregular.
*Prickles.*—Quantity—on main stalks, none; on laterals, none.
*Short needles.*—Quantity—on main stalks, none; on laterals, none.

I claim:

A new and distinct type of bedding rose plant characterized by its hardiness and inflorescence of a true polyantha in combination with the bloom characteristics of a hybrid tea, as shown and described and further characterized as to novelty by color range of the bloom as shown and the resistance of the plant to adverse weather conditions.

SVEND POULSEN.